(12) United States Patent
Martin

(10) Patent No.: US 8,310,468 B2
(45) Date of Patent: Nov. 13, 2012

(54) CONTROL DISPLAY POSITIONING SYSTEM

(75) Inventor: Michael M. Martin, Newport Beach, CA (US)

(73) Assignee: Novartis AG, Basel (CH)

( * ) Notice: Subject to any disclaimer, the term of this patent is extended or adjusted under 35 U.S.C. 154(b) by 1306 days.

(21) Appl. No.: 11/750,083

(22) Filed: May 17, 2007

(65) Prior Publication Data

US 2008/0001866 A1 Jan. 3, 2008

Related U.S. Application Data

(60) Provisional application No. 60/813,615, filed on Jun. 28, 2006.

(51) Int. Cl.
 *G06F 3/038* (2006.01)
 *E04G 3/00* (2006.01)
 *G09G 5/00* (2006.01)
(52) U.S. Cl. .................................. 345/204; 248/274.1
(58) Field of Classification Search .................. 345/204; 248/127–188.91, 200–316.8, 346.01–346.5
See application file for complete search history.

(56) References Cited

U.S. PATENT DOCUMENTS

| | | | |
|---|---|---|---|
| 2,933,803 A | 4/1960 | Schaeffler | |
| 3,072,374 A | 1/1963 | Marcus | |
| 3,160,379 A | 12/1964 | Gardella | |
| 3,366,430 A | 1/1968 | Diedrich | |
| 3,436,046 A | 4/1969 | Valeska | |
| 3,823,906 A | 7/1974 | Rogers | |
| 3,952,849 A | 4/1976 | Brownhill et al. | |
| 4,437,677 A | 3/1984 | Ksayian | |
| 4,625,731 A | 12/1986 | Quedens et al. | |
| 4,695,024 A | 9/1987 | Haven | |
| 4,836,486 A | 6/1989 | Vossoughi et al. | |
| 4,844,387 A | 7/1989 | Sorgi et al. | |
| 4,913,396 A | 4/1990 | Dalebout et al. | |
| 4,989,698 A | 2/1991 | Dony | |
| 5,028,746 A | 7/1991 | Petrich | |
| 5,037,053 A | 8/1991 | Fox et al. | |
| 5,056,866 A | 10/1991 | Tobler | |
| 5,070,976 A | 12/1991 | Zlotek | |
| D325,086 S | 3/1992 | Charles et al. | |
| 5,123,621 A | 6/1992 | Gates | |
| 5,177,616 A | 1/1993 | Riday | |

(Continued)

FOREIGN PATENT DOCUMENTS

DE 20200370 4/2002

(Continued)

OTHER PUBLICATIONS

International Search Report for PCT/US2007/069126, Publication No. WO2008002728, 1 page.

(Continued)

*Primary Examiner* — Srilakshmi K Kumar

(74) *Attorney, Agent, or Firm* — Darien Reddick

(57) ABSTRACT

A control display positioning system includes three vertically oriented hinges and a horizontally oriented hinge attached to the back of the control display. Two arms are used to connect the three vertically oriented hinges one to another. In each vertically oriented hinge is a central space for the passage of electrical cables therethrough. Also in each vertically oriented hinge is a washer stack that provides the necessary friction forces for the control display positioning system to remain in a selected position after being repositioned by a user.

23 Claims, 4 Drawing Sheets

U.S. PATENT DOCUMENTS

| | | | |
|---|---|---|---|
| 5,179,447 | A | 1/1993 | Lain |
| 5,337,869 | A | 8/1994 | Zlotek |
| D352,106 | S | 11/1994 | Fanney et al. |
| 5,398,622 | A | 3/1995 | Lubinskas et al. |
| 5,455,766 | A | 10/1995 | Scheller et al. |
| 5,553,820 | A | 9/1996 | Karten et al. |
| 5,611,513 | A | 3/1997 | Rosen |
| 5,627,584 | A | 5/1997 | Nishikori et al. |
| 5,655,741 | A | 8/1997 | Watkins |
| 5,667,179 | A | 9/1997 | Rosen |
| 5,779,209 | A | 7/1998 | Rello |
| 5,820,253 | A | 10/1998 | Scholz |
| 5,823,120 | A | 10/1998 | Holmquist |
| 5,924,988 | A | 7/1999 | Burris |
| 6,000,560 | A | 12/1999 | Barkan |
| 6,007,036 | A | 12/1999 | Rosen |
| 6,019,332 | A * | 2/2000 | Sweere et al. ............ 248/284.1 |
| 6,022,088 | A | 2/2000 | Metzler |
| 6,024,427 | A | 2/2000 | Underwood et al. |
| 6,076,785 | A | 6/2000 | Oddsen, Jr. |
| 6,102,476 | A | 8/2000 | May et al. |
| 6,145,926 | A | 11/2000 | Lin |
| 6,179,263 | B1 | 1/2001 | Rosen et al. |
| 6,220,658 | B1 | 4/2001 | Lukawski et al. |
| 6,244,779 | B1 | 6/2001 | Slasinski |
| D447,567 | S | 9/2001 | Murphy et al. |
| 6,409,134 | B1 * | 6/2002 | Oddsen, Jr. ............... 248/274.1 |
| 6,447,451 | B1 | 9/2002 | Wing et al. |
| D467,001 | S | 12/2002 | Buczek et al. |
| 6,510,049 | B2 | 1/2003 | Rosen |
| 6,526,896 | B2 | 3/2003 | Woronecki et al. |
| 6,587,333 | B2 | 7/2003 | Tseng et al. |
| 6,626,445 | B2 | 9/2003 | Murphy et al. |
| 6,736,360 | B1 | 5/2004 | Buczek |
| 7,044,568 | B2 | 5/2006 | Olivera et al. |
| D550,362 | S | 9/2007 | Olivera et al. |
| 7,461,825 | B2 | 12/2008 | Olivera et al. |
| 7,630,193 | B2 | 12/2009 | Ledbetter et al. |
| 2001/0035702 | A1 | 11/2001 | Rodriguez et al. |
| 2002/0000505 | A1 | 1/2002 | Cho |
| 2003/0023164 | A1 | 1/2003 | Eichelberger et al. |
| 2004/0195482 | A1 | 10/2004 | Kollar et al. |
| 2005/0152102 | A1 | 7/2005 | Shin |
| 2006/0022102 | A1 | 2/2006 | Dittmer |
| 2006/0065806 | A1 | 3/2006 | Shin |
| 2007/0159035 | A1 | 7/2007 | Mullen |
| 2007/0284495 | A1 | 12/2007 | Charles |
| 2008/0001866 | A1 | 1/2008 | Martin |
| 2008/0033404 | A1 | 2/2008 | Romoda et al. |
| 2008/0123264 | A1 | 5/2008 | Romoda et al. |
| 2008/0132786 | A1 | 6/2008 | Asai et al. |
| 2008/0215982 | A1 | 9/2008 | Washburn et al. |
| 2010/0039380 | A1 | 2/2010 | Lanier et al. |

FOREIGN PATENT DOCUMENTS

| | | |
|---|---|---|
| EP | 1 139 003 A2 | 10/2001 |
| EP | 1 626 222 A2 | 2/2006 |
| JP | 3-7543 | 1/1991 |
| JP | 7191609 | 2/1997 |
| JP | 10-127351 | 5/1998 |
| JP | 2000-139611 | 5/2000 |
| JP | 11-239583 | 3/2001 |
| JP | 2002-510026 | 2/2002 |
| RU | 2158537 | 11/2000 |
| WO | WO 99/50587 | 10/1999 |
| WO | WO 01/45627 | 6/2001 |

OTHER PUBLICATIONS

European Search Report for Application No. 03022415.8, Filed Oct. 6, 2003, Publication No. 1440666, Published Jul. 28, 2004, 2 pages.

European Search Report for Application No. 03077206.5, Filed Jul. 11, 2003, Publication No. 1396235, Published Mar. 10, 2004, 2 pages.

European Search Report for Application No. 07812738.8, Filed Jul. 10, 2007, Publication No. 2061986, Published May 27, 2009, 2 pages.

International Search Report for Application No. PCT/US2007/073106, Filed Jul. 10, 2007, Publication No. WO2008036453, Published Mar. 27, 2008, 1 page.

PCT International Preliminary Report on Patentability and Written Opinion for Application No. PCT/US2007/073106, Filed Jul. 10, 2007, Publication No. WO2008036453, Published Mar. 27, 2008, 6 pages.

International Search Report for PCT/US2007/069126, Publication No. WO2008002728, 1 page, Aug. 27, 2008.

Supplemental European Search Report for Application No. 07797539.9, Publication No. EP2033181, Published Mar. 11, 2009, 2 pages.

PCT International Preliminary Report on Patentability, PCT/US2007/069126, Jan. 6, 2009, 7 pages.

Written Opinion of the International Searching Authority, International Application No. PCT/US2007/069126, Apr. 24, 2008, 6 pages.

* cited by examiner

CONTROL DISPLAY POSITIONING SYSTEM

This application claims the priority of U.S. Provisional Application No. 60/813,615 filed Jun. 28, 2006.

FIELD

The present invention pertains to positioning systems for control displays; more particularly, the present invention pertains to a control display positioning system used with medical/surgical equipment.

BACKGROUND

Prior art medical/surgical systems such as ophthalmic surgical systems with control displays provide limited access to the control display, touch screen, and graphical user interface (GUI). In some medical/surgical systems, the control display is permanently affixed to the front panel of the machine so that it cannot be moved. In other medical/surgical systems, the control display is mounted on a yoke-type device so that the control display can both spin from side to side about a vertical axis and also tilt about a horizontal axis. However, since the display is still centered on and mounted to the medical/surgical system, the health care professional is still restricted to accessing the control display from a position directly in front of the machine.

Restricting the control display to a position directly in front of a medical/surgical system is a problem in a medical/surgical setup where trays of surgical tools and devices must often be placed directly in front of the system. In this configuration, a health professional must reach over the surgical tools and devices to gain access to the control display. Such positioning of the control display risks compromising the sterile field near the machine and over the surgical tools and devices.

Another situation that presents difficulty is accessing the GUI when the patient is positioned between the medical/surgical system and the user. In this situation, the user must reach over the patient to access the GUI.

Yet another problem is accommodating the body position of the health care professional using the medical/surgical system. In some procedures the health care professional is more comfortable working from a sitting position. In other procedures the heath care professional is more comfortable working from a standing position. Whether seated or standing, the height of the health care professional is also a major concern. This is because a health care professional can misread the screen because the screen is not properly positioned to provide a clear line of sight. Misreading the screen could result in an improper and possibly unsafe step in a surgical procedure. Accordingly, the proper placement of a control display with respect to the eyes of a health care professional to avoid glare from the screen, reflections from room lighting, or distortions of the images appearing on the control display is essential.

It has also been found that the pivoting of prior art control display positioning systems into different orientations causes twisting of the cables housed within the control display positioning system. This twisting of the cables places a mechanical stress on the cables. This mechanical stress will eventually cause the cables to break. In some prior art systems the cables leading to a control display are wrapped into tight coils. In other prior art systems, movement of the cables is restricted at each cable end. This restricting of the movement of the cables at each end is done so that the mechanical stress caused by movement of the cable on each axis could be reduced axis by axis.

The problem with the axis by axis restriction on cable movement is that the cables must be quite long because the length of the cable needed to handle the rotation in each axis is additive. The increased cable length is required to be stored in a relatively large coil. The need to store a relatively large coil of cable increases the overall size of the control display positioning system. When several cable movement axes are used in series, the length of the cable necessitates a significant increase in the size of the control display positioning system. It has also been found that using coiled cables and restricting movement of the cable ends is not an acceptable solution when multiple cables are used. Further, it has also been found that it is advantageous to separate video signal transmission cables from other cables to reduce the amount of noise added to the video signal.

Another problem with prior art control display positioning systems is that the spring force, used to push friction generation surfaces together, is typically created by the compression of a series of wave washers. Because individual wave washers provide a relatively low level of force when compressed, several wave washers must be used in series to generate the amount of force needed to press on the friction generation surfaces. Wave washers also are characterized by a linear deflection to force curve (spring rates). As a result, variations in the deflection of the wave washers caused by a variation in the dimensions of the wave washers and their mating parts cause a large variation in spring force. This large variation in spring force, in turn, results in a large variation in frictional force.

Accordingly, there remains a need in the art for a control display positioning system that is usable with a piece of medical/surgical equipment that: a) adjusts the position of the control to display to where it can be best seen by a health care professional; b) reduces the mechanical stress on the electrical cables providing electrical signals to the control display; c) provides a wide range of motion for the control display, and d) retains its position when manually repositioned.

SUMMARY

The control display positioning system of the present invention permits adjusting the position of the control display to a wide variety of positions where it can best be seen by a health care professional; reduces the mechanical stress on the cables providing electrical signals to the control display and retains its position when manually repositioned.

The disclosed control display positioning system features three hinges—each having a substantially vertical axis to provide rotational movement in a substantially horizontal plane. The first or base vertical hinge is mounted to a stationary portion of a piece of medical/surgical equipment. Extending outwardly from the proximal end of the base vertical hinge is a first arm. At the opposite or distal end of the first arm is located the second or elbow vertical hinge. Extending outwardly from the proximal end of the elbow vertical hinge is a second arm. At the distal end of the second arm is located a third or display vertical hinge. Connecting the display vertical hinge to the control display is a control display mounting or horizontal hinge to move the control display with respect to a substantially vertical plane. The horizontal hinge is mounted to the back of the control display.

Within each vertical hinge is a substantially cylindrical passage. The cable bundle which provides electrical signals to the control display passes through this substantially cylindrical passage.

Surrounding the substantially cylindrical passage within each vertical hinge is a friction mechanism for holding each vertical hinge in a selected position. The friction mechanism for holding each vertical hinge in a selected position includes a stack of washers. Friction forces are created by the contact between a friction washer and a steel washer. The force pushing the friction washer and the steel washer together is provided by a stack of one or more Belleville washers.

BRIEF DESCRIPTION OF THE DRAWING FIGURES

A still better understanding of the control display positioning system of the present invention may be had by reference to the drawing figures wherein.

DESCRIPTION OF THE EMBODIMENTS

Figure 1:
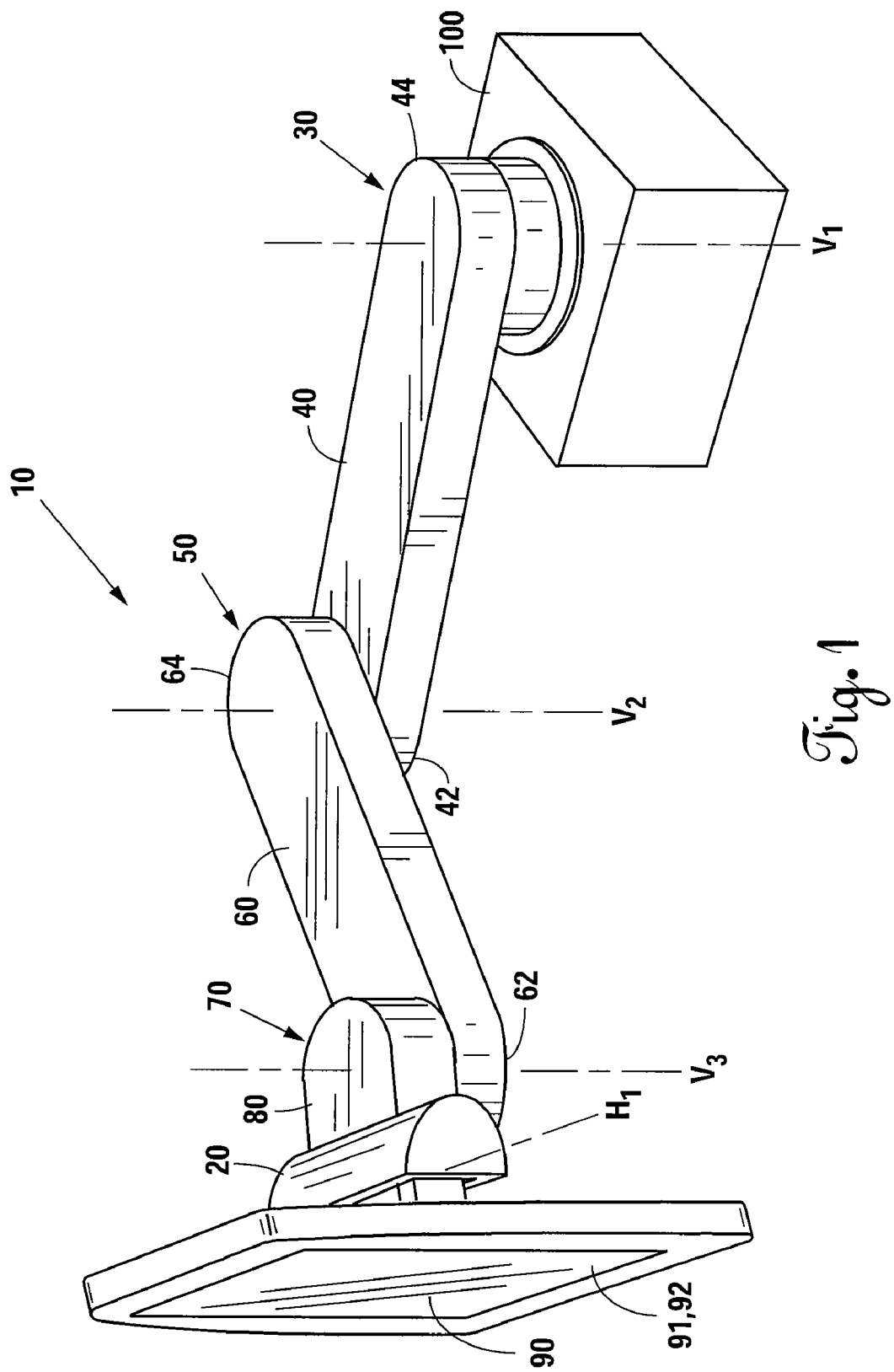
FIG. 1 is a perspective view of the control display positioning system of the present invention mounted to a stationary portion of a piece of medical/surgical equipment.

The disclosed control display positioning system 10 as shown in FIG. 1 is used to support and position a control display 90 for a medical/surgical system 100 such as an ophthalmic surgical system. Those of ordinary skill in the art will understand that the disclosed system 10 may also be used with other types of medical/surgical equipment.

An important feature of the disclosed system 10 is that the cables 110 which deliver electrical energy and signals to the electronic components housed within the control display 90 are contained within the control display positioning system 10. Another feature of the disclosed control display positioning system 10 is that the frictional force within the hinges 20, 30, 50, 70 keeps the control display 90 at any selected position. The health care professional repositions the control display 90 simply by applying sufficient force to overcome the frictional force within the hinges 20, 30, 50, 70. The result is that the disclosed control display positioning system 10 enables the control display 90 to be placed and remain in any position within a semi-circular area about the front or either side of the medical/surgical system 100.

The control display 90 includes a graphical user interface (GUI) 91 having a touch panel or touch screen 92. It is the touch panel 92 which acts as the primary user input device for the system 100. The 4 axis arm movement of the disclosed control display positioning system 10 allows the control display 90 to be located in positions ranging from the center of the machine, to over the patient, to a position extended out in front of or to the sides of the piece of medical/surgical equipment. This increased range of motion facilitates access to the display by nurses who may be acting in several different operational roles during a medical/surgical procedure.

The disclosed control display positioning system 10 includes 3 vertical spin axes $V_1$, $V_2$, $V_3$ through each hinge 30, 50, 70 and one horizontal tilt axis $H_1$, through the remaining hinge 20. The 3 vertical spin axes $V_1$, $V_2$, and $V_3$ allow the disclosed control display positioning system 10 to move the control display 90 to any position in a horizontal plane parallel to the floor within its range of motion. The horizontal tilt axis $H_1$ provided by the hinge 20 allows the viewing angle of the display 90 to be adjusted by ±20° with respect to a vertical plane to accommodate users of different heights.

Figure 2A:
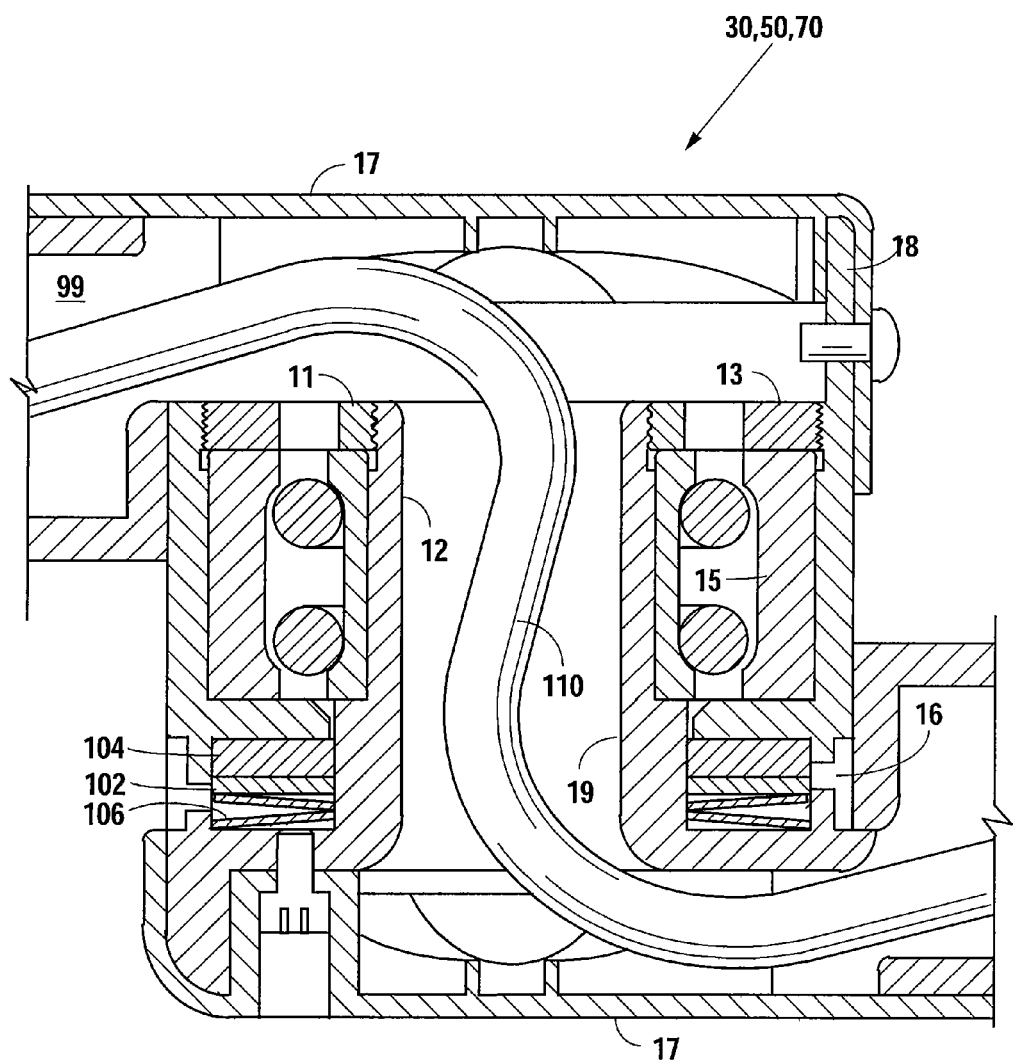
FIG. 2A is a side, sectional of the vertically oriented hinge used in the disclosed invention.
Figure 2B:
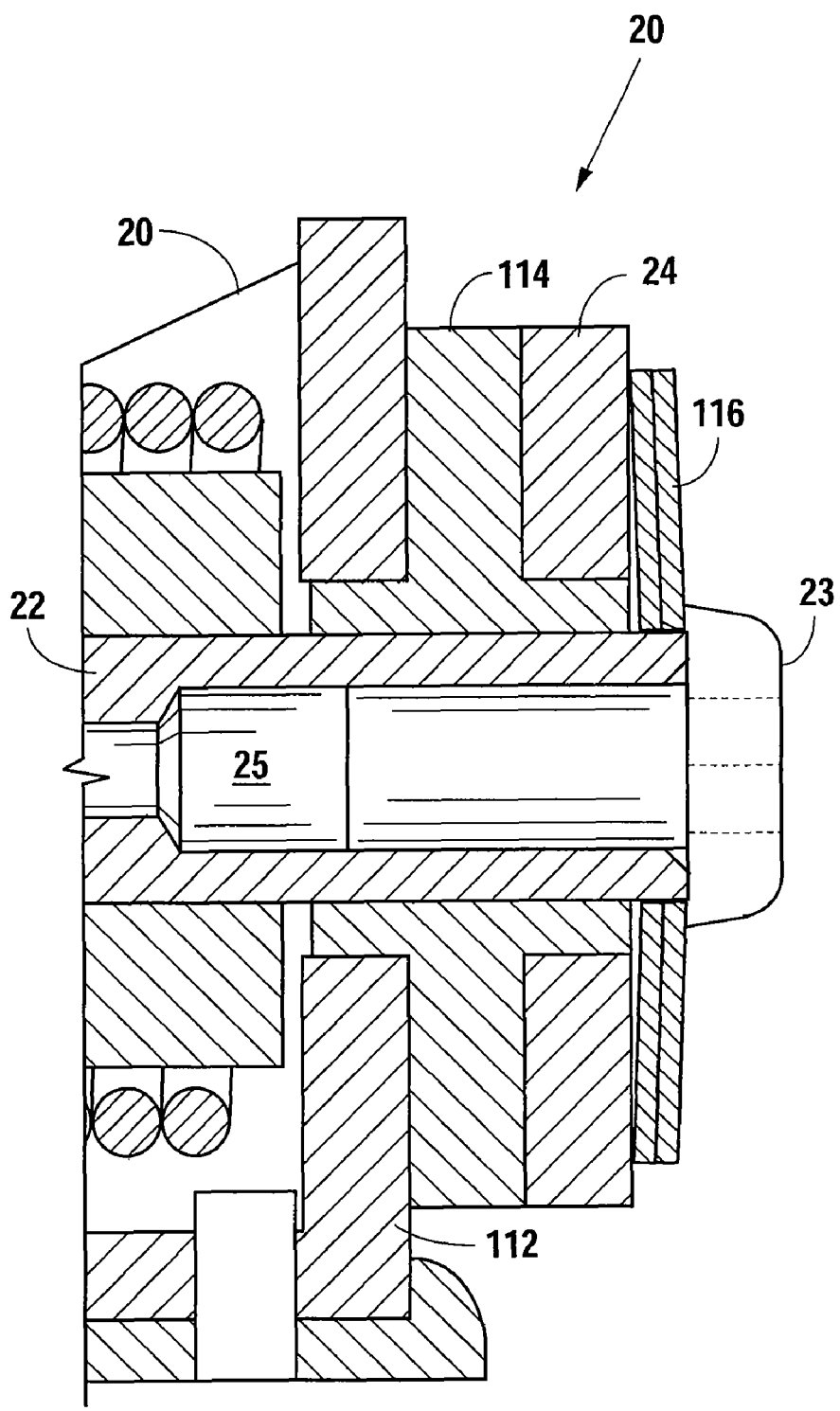
FIG. 2B is a side, sectional view of the horizontally oriented hinge used in the disclosed invention.

Both the vertically oriented hinges 30, 50, 70 and the horizontally oriented hinge 20 have friction generating mechanisms as shown generally in FIGS. 2A and 2B, respectively, to create drag and allow each arm 40 and 60 to remain in position once placed there. In the vertical axes $V_1$, $V_2$, $V_3$, friction is created by pressing a stainless steel washer 102 against a plastic friction washer 104 as shown in FIG. 2A. Belleville washers 106 that have a non-linear spring constant are used to create the load on washer 102. The Belleville washers 106 reduce the fluctuation in frictional load.

It has been found that more consistent frictional force is achieved by using Belleville washers 106 with nonlinear spring rates. The Belleville washers 106 selected for use in the disclosed invention are specifically designed so that the deflection is in a very flat section of their force curve. The result is that variations in the deflection caused by stacked up tolerance variations result in very small changes in the normal force applied to the friction washer 104.

Included within each vertical hinge assembly is an inner race spanner nut 11, an outer race spanner nut 13 and a ball bearing 15. While a ball bearing 15 has been used in the preferred embodiment, those of ordinary skill in this will understand that other types of bearings may be used without departing from the scope of the invention. At the bottom of each vertical hinge assembly is a rotation limitation ring 16. One or more caps or covers 17 may be included to keep dirt and debris out of the hinge assembly. Hinge assemblies 30, 50 and 70 are each contained within a housing 18 that is rotationally coupled to outer race spanner nut 13. Hinge assemblies 30, 50 and 70 each have a hinge shaft 19 that is rotationally coupled to inner race spanner nut 11. The rotation of hinges 30 and 70 is limited to 180°; while the rotation of hinge 50 is a full 360°.

The display vertical hinge assembly 70 is attached to the distal end 62 of the first arm 60. At the opposite end 64 of the first arm 60 is located the elbow vertical hinge assembly 50. The elbow vertical hinge assembly 50 provides a connection between the end 64 of the first arm 60 and the distal end 42 of the second arm 40. At the opposite end 44 of the second arm 40 is located the base vertical hinge assembly 30. The base vertical hinge assembly 30 is connected to a stationary portion of medical/surgical system 100.

There is sufficient space within each hinge assembly 30, 50, 70 so that several cables may be routed through the center bore 12 of the hinges. These cables may include an LVDS Signal Cable, an interface data cable, and a cable grouping strap. By allowing the cables to pass in an unrestricted manner through the center bore 12 of the hinge assemblies 30, 50, 70 at all 3 spin axes, mechanical stress in the cables and the resulting cable failure is reduced.

Figure 3:
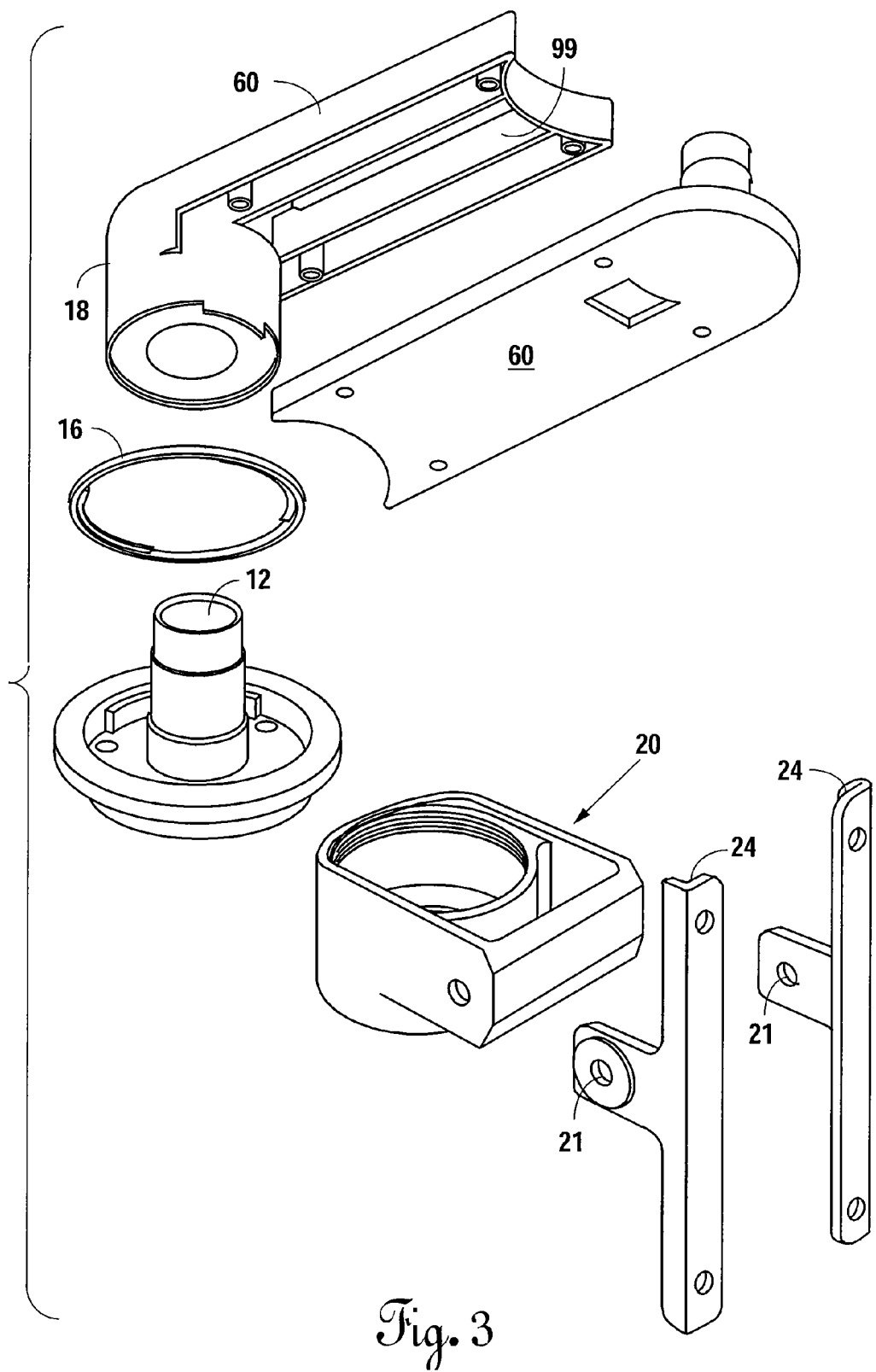
FIG. 3 is an exploded perspective view of the horizontally oriented hinge attached to the back of the control display for tilting the control display with respect to a vertical plane and the display mounting vertical hinge.

Cable length and cable stress is further reduced by running the cable through an open space 99 running the length of each arm 40, 60 as shown in FIG. 3. This reduction of cable stress occurs for two reasons. First, by allowing the path for cable travel to be unrestricted between vertical axes, the twisting motion of one axis can cancel out the opposing twisting motion of a neighboring axis. Additionally, leaving the path 99 for cable travel unrestricted throughout the entire length of each arm 40, 60 allows for a greater cable length. This greater cable length allows for any given annular deflection to be distributed over a longer section of cable thus reducing any mechanical stress concentration in the cable. If the cable were strain-relieved at either end of each axis as in prior art systems, the angular deflection would to be concentrated over only a couple of inches of cable. It has been found that by strain-relieving the cable at the beginning and at the end of the series of axes, the length that the angular deflection may be distributed over is increased to over 12 inches.

Referring to FIG. 3, there are two vertical bars 24 on which the control display 90 is mounted. Bars 24 are connected to the control display mounting or horizontal hinge assembly 20, which provides tilting of the control display 90 about a substantially horizontal axis. Horizontal hinge assembly 20 is connected to display vertical hinge assembly 70.

By comparing FIG. 3 to FIG. 2B, it may be seen that shaft 22 passes through holes 21 in each vertical bar 24. Each end of the shaft 22 receives a screw 23 within an internally threaded portion 25. Horizontal hinge assembly 20 further includes a stainless steel shim washer 112, a plastic friction washer 114, and a set of Belleville washers 116. Tightening of the screw 23 compresses Belleville washers 116 against bar 24 and friction washer 114 to provide the necessary frictional force to maintain the tilt of the control display 90 about the horizontal axis $H_1$. Similar to Belleville washers 106 in hinge assemblies 30, 50, and 70, Belleville washers 116 have a non-linear spring constant that reduce the fluctuation in frictional load.

While the disclosed control display positioning system has been disclosed according to its preferred embodiment, those of ordinary skill in the art will understand that numerous other embodiments have been enabled by the foregoing disclosure. Such other embodiments shall be included within the scope and meaning of the appended claims.

What is claimed is:

1. A control display positioning system for use with a medical/surgical system, said control display positioning system comprising:
   a control display mounting constructed and arranged for permitting tilting of a control display about a substantially horizontal axis;
   said control display mounting being connected to a display vertical hinge assembly constructed and arranged for turning about a substantially vertical axis;
   said display vertical hinge assembly being connected to the distal end of a first arm;
   an elbow hinge assembly constructed and arranged for turning about a substantially vertical axis;
   said elbow hinge assembly being connected to the proximal end of said first arm and at the distal end of a second arm;
   a base hinge assembly constructed and arranged for turning about a substantially vertical axis;
   said base hinge assembly being connected to the proximal end of said second arm;
   wherein said display vertical hinge assembly, said elbow hinge assembly and said base hinge assembly include:
      a space to enable the passage of a cable bundle therethrough; and
      a set of washers to provide friction forces within each hinge assembly sufficient to enable each hinge assembly to maintain its position,
   wherein at least one of the display vertical hinge assembly, the elbow hinge assembly, or the base hinge assembly comprises:
      a shaft rotationally coupled to an inner spanner nut;
      an outer spanner nut rotationally coupled to an outer hinge housing; and
      a ball bearing located between the inner spanner nut and the outer spanner nut on one side and the set of washers on an opposing side.

2. The control display positioning system as defined in claim 1 wherein said control display mounting provides for tilting about +/−20° from a vertical plane.

3. The control display positioning system as defined in claim 1 wherein said set of washers includes a friction washer, a steel washer, and at least one Belleville washer.

4. The control display positioning system as defined in claim 3 wherein said at least one Belleville washer is selected to provide a nonlinear force to deflection relationship to said set of washers.

5. The control display positioning system as defined in claim 1 wherein the rotation of said display hinge assembly and the rotation of said base hinge assembly are limited to about 180°.

6. The control display positioning system as defined in claim 1 wherein the control display mounting includes a second set of washers to provide friction forces to enable said control display mounting to maintain its position.

7. The control display positioning system as defined in claim 6 wherein said second set of washers includes a friction washer and at least one Belleville washer.

8. The control display positioning system as defined in claim 7 wherein said at least one Belleville washer is selected to provide a nonlinear force to deflection relationship to said second set of washers.

9. A medical/surgical system comprising:
   a base unit;
   a control display;
   a positionable arm assembly connecting said base unit to said control display;
   said positionable arm assembly including:
      a display tilting hinge having a substantially horizontal axis;
      a display mounting hinge having a substantially vertical axis;
      a central elbow hinge having a substantially vertical axis;
      a base hinge having a substantially vertical axis;
      a first arm connecting said display mounting hinge and said central elbow hinge;
      a second arm connecting said central elbow hinge and said base hinge; and
      a washer stack in said display mounting hinge, in said central elbow hinge; and in said base hinge for creating a frictional force to maintain the configuration of said positionable arm assembly after manual re-positioning,
   wherein at least one of the display mounting hinge, the central elbow hinge, or the base hinge comprises:
      a shaft rotationally coupled to an inner spanner nut;
      an outer spanner nut rotationally coupled to an outer hinge housing; and
      a ball bearing located between the inner spanner nut and the outer spanner nut on one side and the washer stack on an opposing side.

10. The medical/surgical system as defined in claim 9 wherein said display tilting hinge provides for tilting said control display about +/−20° from a vertical plane.

11. The medical/surgical system as defined in claim 9 wherein said washer stack includes a friction washer, a steel washer and at least one Belleville washer.

12. The medical/surgical system as defined in claim 9 wherein said display mounting hinge, said central elbow hinge and said base hinge include a central passage to enable the passage of a cable therethrough.

13. The medical/surgical system as defined in claim 9 wherein the rotation of said display mounting hinge and the rotation of said base hinge are limited to about 180°.

14. The medical/surgical system as defined in claim 9 further comprising a second washer stack in said display tilting hinge for creating a frictional force to maintain the configuration of said display tilting hinge after manual repositioning.

15. The medical/surgical system as defined in claim 14 wherein said second washer stack includes a friction washer and at least one Belleville washer.

16. A method for positioning a control display with respect to a medical/surgical system comprising the steps of:
    attaching the control display to a display hinge having a substantially horizontal axis to enable tilting of the control display about said horizontal axis;
    attaching said display hinge to a display mounting hinge having a substantially vertical axis to enable rotation of the control display about said vertical axis;
    attaching said display mounting hinge to an elbow hinge having a substantially vertical axis to enable rotation of said display hinge about said vertical axis;
    attaching said elbow hinge to a base hinge having a substantially vertical axis to enable rotation of the elbow hinge about said vertical axis; and
    attaching said base hinge to a stationary portion of the medical/surgical system,
    wherein said display mounting hinge, said elbow hinge and said base hinge each include a washer stack, said washer stack comprising a friction washer, a steel washer, and a Belleville washer,
    wherein at least one of the display hinge, the display mounting hinge, or the elbow hinge comprises:
        a shaft rotationally coupled to an inner spanner nut;
        an outer spanner nut rotationally coupled to an outer hinge housing; and
        a ball bearing located between the inner spanner nut and the outer spanner nut on one side and the washer stack on an opposing side.

17. The method as defined in claim 16 wherein said control display is tiltable +/−20° with respect to a vertical plane.

18. The method as defined claim 16 wherein said display mounting hinge, said elbow hinge and said base hinge each have a passageway constructed and arranged for the passage of a cable therethrough.

19. The method as defined in claim 16 wherein the rotation of said display mounting hinge and said base hinge are limited to about 180°.

20. The method as defined in claim 16 wherein said display hinge uses a washer stack, said washer stack including a friction washer and a Belleville washer.

21. The control display positioning system of claim 3, wherein the friction washer, the steel washer, and the at least one Bellville washer are coaxially arranged.

22. The medical/surgical system of claim 11, wherein the friction washer, the steel washer, and the at least one Bellville washer are coaxially arranged.

23. The method of claim 16, wherein the friction washer, the steel washer, and the Bellville washer are coaxially arranged.

* * * * *